US012766495B2

(12) United States Patent
Liu et al.

(10) Patent No.: US 12,766,495 B2
(45) Date of Patent: Oct. 20, 2026

(54) HYDROGENATION CATALYST AND PREPARATION METHOD THEREFOR AND USE THEREOF, AND HYDROGENATION REACTION METHOD FOR OIL PRODUCTS

(71) Applicants: CHINA PETROLEUM & CHEMICAL CORPORATION, Beijing (CN); SINOPEC DALIAN RESEARCH INSTITUTE OF PETROLEUM AND PETROCHEMICALS CO., LTD., Dalian (CN)

(72) Inventors: Li Liu, Dalian (CN); Chengmin Yang, Dalian (CN); Bumei Zheng, Dalian (CN); Rong Guo, Dalian (CN); Weiyu Duan, Dalian (CN); Yunhai Yao, Dalian (CN); Xiaozhen Chen, Dalian (CN); Jin Sun, Dalian (CN); Xiaoying Yin, Dalian (CN)

(73) Assignees: CHINA PETROLEUM & CHEMICAL CORPORATION, Beijing (CN); SINOPEC DALIAN RESEARCH INSTITUTE OF PETROLEUM AND PETROCHEMICALS CO., LTD., Dalian (CN)

( * ) Notice: Subject to any disclaimer, the term of this patent is extended or adjusted under 35 U.S.C. 154(b) by 221 days.

(21) Appl. No.: 18/705,928

(22) PCT Filed: Oct. 26, 2022

(86) PCT No.: PCT/CN2022/127557

§ 371 (c)(1),
(2) Date: Apr. 29, 2024

(87) PCT Pub. No.: WO2023/072117

PCT Pub. Date: May 4, 2023

(65) Prior Publication Data

US 2025/0319460 A1 Oct. 16, 2025

(30) Foreign Application Priority Data

Oct. 31, 2021 (CN) ........................ 202111278954.5

(51) Int. Cl.
*B01J 21/06* (2006.01)
*B01J 21/04* (2006.01)
(Continued)

(52) U.S. Cl.
CPC ........... *B01J 37/0207* (2013.01); *B01J 21/04* (2013.01); *B01J 29/166* (2013.01); *B01J 29/48* (2013.01);
(Continued)

(58) Field of Classification Search
CPC . B01J 27/051; B01J 6/001; B01J 21/04; B01J 23/75; B01J 23/755; B01J 37/0201;
(Continued)

(56) References Cited

U.S. PATENT DOCUMENTS 4,435,278 A * 3/1984 Chen ........................ B01J 35/60 502/220
2002/0082165 A1 6/2002 Kasztelan et al.
(Continued)

FOREIGN PATENT DOCUMENTS

CN 1778873 A 5/2006
CN 1778874 A 5/2006
(Continued)

OTHER PUBLICATIONS

Liu, Xiaozhan et al.; "Ni—Mo Sulfide Semiconductor Catalyst with High Catalytic Activity for One-Step Conversion of CO2 and H2S to Syngas in Non-Thermal Plasma"; Catalysts; vol. 9, No. 525; Jun. 12, 2019; pp. 1-13.
(Continued)

*Primary Examiner* — Tam M Nguyen
(74) *Attorney, Agent, or Firm* — NKL Law; Allen Xue

(57) ABSTRACT

A hydrogenation catalyst and a preparation method therefor and the use thereof, and a hydrogenation reaction method for oil products are presented. The hydrogenation catalyst is a
(Continued)

sulfurized hydrogenation catalyst and comprises a carrier, a molecular sieve and an active component, wherein the active component comprises at least one of group VIII metal elements and at least one of group VIB metal elements, and is characterized by using a TEM-EDS method. On the basis of the silicon element, the ratio of the amount of the molecular sieve directly acting on a group VIB metal sulfide to the total amount of the molecular sieve is 60-100%. The hydrogenation catalyst provided in the present invention can control a polycyclic aromatic hydrocarbon to realize ring opening without chain scission, generating a monocyclic aromatic hydrocarbon with a long-branched chain, which can be used as both an ethylene cracking raw material and a diesel product.

20 Claims, 1 Drawing Sheet

(51) Int. Cl.

| | |
|---|---|
| ***B01J 29/16*** | (2006.01) |
| ***B01J 29/48*** | (2006.01) |
| ***B01J 29/78*** | (2006.01) |
| ***B01J 37/00*** | (2006.01) |
| ***B01J 37/02*** | (2006.01) |
| ***B01J 37/04*** | (2006.01) |
| ***B01J 37/06*** | (2006.01) |
| ***B01J 37/10*** | (2006.01) |
| ***B01J 37/20*** | (2006.01) |
| ***C07C 5/11*** | (2006.01) |

(52) U.S. Cl.

CPC ........... *B01J 29/78* (2013.01); *B01J 29/7815* (2013.01); *B01J 37/009* (2013.01); *B01J 37/0236* (2013.01); *B01J 37/04* (2013.01); *B01J 37/06* (2013.01); *B01J 37/10* (2013.01); *B01J 37/20* (2013.01); *C07C 5/11* (2013.01)

(58) Field of Classification Search

CPC ........ B01J 37/04; B01J 37/20; B01J 2235/00; B01J 2235/30; B01J 21/12; B01J 23/882; B01J 23/883; B01J 27/0515; B01J 37/0018; B01J 37/0203; B01J 37/0205; B01J 37/0207; B01J 37/086; B01J 37/088; B01J 23/002; B01J 2523/00; C01P 2002/72; C01P 2002/85; C01P 2004/04; C10G 2400/04; C10G 45/08; C10G 2300/202; C01G 39/006; C01G 51/82

See application file for complete search history.

(56) References Cited

U.S. PATENT DOCUMENTS

| | | | | |
|---|---|---|---|---|
| 2013/0165316 | A1 | 6/2013 | Guichard et al. | |
| 2016/0030934 | A1 | 2/2016 | Zhan et al. | |
| 2016/0263563 | A1 | 9/2016 | Liu et al. | |
| 2018/0126362 | A1 | 5/2018 | Bus et al. | |
| 2019/0232269 | A1 | 8/2019 | Zhang et al. | |
| 2022/0362751 | A1* | 11/2022 | Liu | B01J 21/04 |

FOREIGN PATENT DOCUMENTS

| | | | | | |
|---|---|---|---|---|---|
| CN | 1854262 | A | | 11/2006 | |
| CN | 101254471 | A | | 9/2008 | |
| CN | 102471700 | A | | 5/2012 | |
| CN | 103666553 | A | | 3/2014 | |
| CN | 104646052 | A | | 5/2015 | |
| CN | 106179467 | A | | 12/2016 | |
| CN | 106669786 | A | | 5/2017 | |
| CN | 108014781 | A | * | 5/2018 | B01J 23/002 |
| CN | 109569699 | A | | 4/2019 | |
| CN | 110038617 | A | | 7/2019 | |
| CN | 111760585 | A | | 10/2020 | |
| CN | 112657539 | A | | 4/2021 | |
| CN | 112705225 | A | * | 4/2021 | B01J 27/0515 |
| CN | 112717982 | A | | 4/2021 | |
| FR | 2778341 | A1 | | 11/1999 | |
| JP | 2001246253 | A | | 9/2001 | |
| RU | 2641702 | C2 | | 1/2018 | |
| RU | 2715424 | C2 | | 2/2020 | |
| RU | 2019106451 | A | | 10/2020 | |
| WO | 2006028878 | A1 | | 3/2006 | |

OTHER PUBLICATIONS

Liu, Li et al.; "Study on properties of Diesel Hydrodesulfurization Catalyst with Mesoporous ZSM-5 Zeolite"; Petroleum Refining and Chemical Industry; vol. 29, No. 9; Sep. 2018; pp. 54-58.

* cited by examiner

HYDROGENATION CATALYST AND PREPARATION METHOD THEREFOR AND USE THEREOF, AND HYDROGENATION REACTION METHOD FOR OIL PRODUCTS

CROSS-REFERENCE TO RELATED APPLICATIONS

This application is a U.S. national stage entry of PCT International Application No. PCT/CN2022/127557, filed on Oct. 26, 2022, which claims the benefit of Chinese patent application No. "202111278954.5", filed on Oct. 31, 2021, the content of which is incorporated herein by reference in its entirety.

TECHNICAL FIELD

The present invention belongs to the technical field of oil product hydrogenation, and relates to a hydrogenation catalyst and a preparation method and use thereof, and a hydrogenation reaction method for oil products.

BACKGROUND ART

The oil products are generally required for hydrotreatment in the process of processing oil products according to the requirements of product quality, for example, according to the China National Standard VI or European Standard VI for diesel oil, the content of polycyclic aromatic hydrocarbon in the diesel oil product is required to be not more than 7% or not more than 8%, and the polycyclic aromatic hydrocarbon needs to be subjected to hydrogenation saturation; for example, to hydro-upgrading of diesel, it is required to reduce the aromatic hydrocarbon content in diesel and increase the cetane number of diesel oil products; for instance, the special oil product hydrogenation requires to substantially reduce the content of aromatic hydrocarbon in the special oils; for example, the output of naphtha is raised by increasing the production of chemical raw materials, and the hydrocracking is required to increase the output of naphtha. Among the procedures, molecular sieve-containing hydrogenation catalysts are generally used. CN200810104303.2 discloses a modified molecular sieve-based noble metal catalyst for deep aromatic saturation of diesel and a preparation method thereof, the catalyst is suitable for aromatic saturation of the FCC diesel, particularly suitable for deep aromatic saturation of diesel after hydro-upgrading of the FCC diesel. The dearomatized diesel can be used as a blend component of high-quality diesel. The catalyst contains modified HY molecular sieve as carriers and noble metals such as Pt, Pd and Ir as active components. The industrialized HY molecular sieve is modified to have a microporous-mesoporous structure, and the carrier material has medium acidity and is doped with Cr, Zn, Sn and Mo oxides of the active components with ring-opening selectivity, so that the catalyst is characterized in deep cracking inhibition and selective ring-opening. The catalyst is used in the deep aromatic saturation of the second stage in the two-stage hydro-upgrading of diesel. The catalyst can be used for the deep aromatic saturation of diesel, but the carrier of said catalyst is high content of molecular sieve having a high price, and the active metal is the expensive noble metal, thus the catalyst is excessively expensive; in addition, the catalyst has the high content of molecular sieve carrier, wherein most molecular sieve carrier does not play a role.

CN201210332369.3 discloses a method of hydro-conversion of polycyclic aromatic hydrocarbons, the method comprises the following steps: (1) in at least one hydrogenation reaction zone, enabling a material containing polycyclic aromatic hydrocarbons to contact with a hydrogenation catalyst for reaction in the presence of a hydrogen gas to obtain a reaction product with polycyclic aromatic hydrocarbons which are partly hydro-generated and saturated; and (2), in at least one hydrogen-cracking reaction zone, enabling the reaction product with polycyclic aromatic hydrocarbons partly hydro-generated and saturated, which is obtained in the step (1) to contact with a hydrogen-cracking catalyst for reaction in the presence of the hydrogen gas, wherein a conversation rate of the polycyclic aromatic hydrocarbons in the material containing the polycyclic aromatic hydrocarbons is over 40 wt. % by selecting the hydrogenation catalyst and operation conditions of the hydrogenation reaction zone; and relative yield of a monocyclic hydrogenation product in the products is within a range of 4-80%; and the conversion rate of the polycyclic aromatic hydrocarbons based on the total amount of the polycyclic aromatic hydrocarbons in the material containing the polycyclic aromatic hydrocarbons is over 85 wt. % by selecting the hydro-cracking catalyst and the operation conditions in the hydrogen-cracking reaction zone, and the relative yield of the monocyclic hydrogen-cracking product in the products is within a range of 4%-30%. The method of hydro-conversion of the polycyclic aromatic hydrocarbons adopts two catalysts for grading, and the molecular sieve in the carrier of the hydrocracking catalyst is added into the carrier by using a mixing method, most of the molecular sieve is wrapped by alumina and cannot perform the function, such that the performance of the hydrocracking catalyst is influenced.

SUMMARY OF THE INVENTION

In order to overcome the problem in the prior art that the performance of the hydrogenation catalyst and the utilization rate of a metal active component needs to be further improved, the present invention provides a hydrogenation catalyst and a preparation method thereof and use thereof, and a hydrogenation reaction method for oil products. The hydrogenation catalyst provided in the present invention has relatively high activity and selectivity, and can control a polycyclic aromatic hydrocarbon to realize ring opening without chain scission, so as to generate a monocyclic aromatic hydrocarbon with a long-branched chain, which can be used as both an ethylene cracking raw material and a high-quality diesel product.

The first aspect of the present invention provides a hydrogenation catalyst, the hydrogenation catalyst is a sulfurized hydrogenation catalyst and comprises a carrier, a molecular sieve and an active component, wherein the active component comprises at least one of group VIII metal elements and at least one of group VIB metal elements, the hydrogenation catalyst is characterized by using a TEM-EDS method, on the basis of the silicon element, the percentage of the amount of the molecular sieve directly acting on a group VIB metal sulfide relative to the total amount of the molecular sieve is within a range of 60-100%.

Preferably, the molecular sieve is contained in an amount of 1-20 wt. %, more preferably 1-12 wt. %, further preferably 1.5-8 wt. %, based on the total weight of the catalyst.

The second aspect of the present invention provides a preparation method of a hydrogenation catalyst, the method comprises the following steps:

(1) impregnating a carrier with a solution containing an organic auxiliary agent, drying and roasting the carrier in an inert atmosphere to obtain a pretreated carrier;

(2) introducing a VIB group metal salt and a VIII group metal salt into the pretreated carrier through an impregnation method, then sulfurizing the pretreated carrier to obtain a catalyst precursor;

(3) introducing a molecular sieve into the catalyst precursor, subsequently drying and roasting.

The third aspect of the present invention provides a use of the hydrogenation catalyst of the first aspect or the hydrogenation catalyst produced with the method of the second aspect in the oil product hydrogenation.

The fourth aspect of the present invention provides a hydrogen reaction method for oil products, the method comprises subjecting the oil products to contacting and reacting with the hydrogenation catalyst of the first aspect or the hydrogenation catalyst produced with the method of the second aspect.

Preferably, the oil products comprise a polycyclic aromatic hydrocarbon, and the hydrogenation reaction comprises a polycyclic aromatic hydrocarbon hydrogenation saturation reaction.

Compared with the prior art, the technical scheme provided by the present invention has the following advantages:

(1) The catalyst of the present invention comprises a carrier, a molecular sieve and an active component, and more molecular sieves directly act on the activity metal, such that the utilization rate of the molecular sieves and the activity metal is higher, the molecular sieves and the activity metal desirably perform the active role, and it is conducive to reducing the dosage of the molecular sieves and decreasing cost of the catalyst.

(2) The preparation method provided by the present invention can be used for preparing the catalyst through the sequence of carrier pretreatment-loading the activity metal-sulfurization-loading the molecular sieve, so that more molecular sieves directly act on the activity metal and the active function is desirably performed.

(3) The preparation method provided by the present invention is directly sulfurized after being impregnated of active metal and dried, and can be carried out without roasting process, such that the interaction between the metal oxide and the carrier is reduced, and the process is simplified.

DESCRIPTION OF THE PREFERRED EMBODIMENT

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

Unless otherwise specified in the present invention, the percentage and percentage content are calculated in terms of the mass.

The first aspect of the present invention provides a hydrogenation catalyst, the hydrogenation catalyst is a sulfurized hydrogenation catalyst and comprises a carrier, a molecular sieve and an active component, wherein the active component comprises at least one of group VIII metal elements and at least one of group VIB metal elements, the hydrogenation catalyst is characterized by using a TEM-EDS method, on the basis of the silicon element, the percentage of the amount of the molecular sieve directly acting on a group VIB metal sulfide relative to the total amount of the molecular sieve is within a range of 60-100%, preferably within a range of 65-95%, more preferably within a range of 70-90%, and most preferably within a range of 80-90%.

The ratio of the amount of the molecular sieve directly acting on a group VIB metal sulfide in the hydrogenation catalyst provided by the present invention relative to the total amount of the molecular sieve is obviously higher than that of the catalyst provided in the prior art, such that the utilization rate of the molecular sieves and the activity metal is higher, the molecular sieves and the activity metal desirably perform the active role, and it is conducive to reducing the dosage of the molecular sieves and decreasing cost of the catalyst.

In the present invention, the molecular sieve directly acting on a group VIB metal sulfide refers to the molecular sieve loaded on the crystal plate surface of a group VIB metal sulfide.

Figure 1:
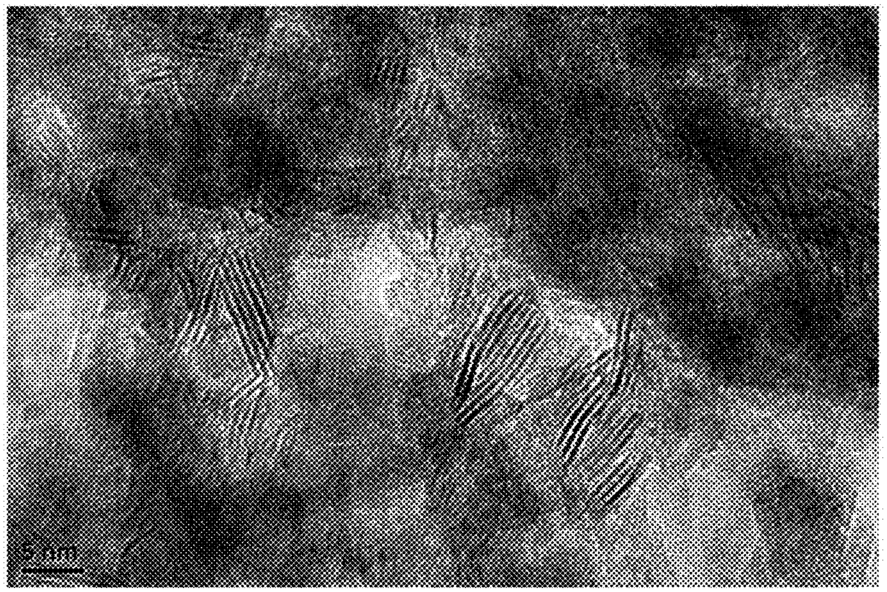
FIG. 1 illustrates a high-resolution transmission electron microscope photograph of the catalyst prepared in Example 1 of the present invention.

In the present invention, in terms of the percentage of the amount of the molecular sieve directly acting on a group VIB metal sulfide relative to the total amount of the molecular sieve, the total amount of the molecular sieve (calculated on the basis of the silicon element) represents the total content of the molecular sieve in the catalyst, the amount of the molecular sieve directly acting on a group VIB metal sulfide refers to the content of the molecular sieve (calculated on the basis of the silicon element) within 2 nm of the outermost layer of the group VIB metal sulfide crystal plate. The percentage of the amount of the molecular sieve directly acting on a group VIB metal sulfide relative to the total amount of the molecular sieve is characterized and obtained by a TEM-EDS (Transmission Electron Microscopy-Energy Dispersive X-ray Spectrum) method, the adopted instrument model is the JEM2200FS type emission transmission electron microscope manufactured by the JEOL Ltd. in Japan, the instrument is provided with a scanning transmission accessory and an X-ray energy spectrum accessory manufactured by the EDAX CORPORATION in the United States of America (USA). In the STEM mode with an accelerating voltage of 200 KV of the electron microscope, the concentrator diaphragm is 2, and the Spote size is 0.5 nm. The measurement process is as follows: grinding the catalyst particles, preparing samples by adopting a suspension method, putting 0.1 g of the catalyst sample into a 2 mL container, performing ultrasonic dispersion by using absolute ethyl alcohol, taking the supernatant, extracting 2-3 droplets by using a dropper, dripping the 2-3 droplets on a sample net having a diameter of 3 mm, drying to obtain a sample to be detected, then observing and analyzing the sample to be detected by using a TEM, then carrying out the statistic analysis on the Si content at a position less than 2 nm away from an edge endpoint on an activity phase (group VIB metal sulfide crystal plate, as shown in FIG. 1) observed by the TEM by combining the EDS, and obtaining the percentage of the amount of the molecular sieve directly acting on a group VIB metal sulfide relative to the total amount of the molecular sieve calculated based on the corresponding peak area of Si. The percentage of the amount of the molecular sieve directly acting on a group VIB metal sulfide relative to the total amount of the molecular sieve in the present invention is obtained by selecting 40 TEM images and averaging the data obtained in combination with the EDS analysis.

The present invention has wide selection ranges of the types and the contents of the molecular sieves in the catalyst, both can be properly selected according to different hydrogenation reactions, and the various hydrogenation purposes can be achieved by controlling the types and the contents of the molecular sieves, for example, the hydrogenation saturation and the ring-opening chain scission activity of the polycyclic aromatic hydrocarbons can be accurately regulated by controlling the types and the contents of the molecular sieves, thus the catalyst flexibility is high.

According to a preferred embodiment of the present invention, the molecular sieve is contained in an amount of 1-20 wt. %, preferably 1-12 wt. %, more preferably 1.5-8 wt. %, most preferably 2-6 wt. %, based on the total weight of the catalyst. The present invention improves the utilization rate of the molecular sieve by increasing the percentage of the amount of the molecular sieve directly acting on a group VIB metal sulfide relative to the total amount of the molecular sieve so that the catalyst can exert better hydrogenation performance even under the condition of lower molecular sieve content, it is beneficial to reducing the cost of the catalyst.

The present invention does not impose specific limitations on the method for measuring the molecular sieve content of the catalyst, the molecular sieve content can be determined by combining the amount of the silicon oxide with the crystal form of the molecular sieve measured by XRD (X-ray diffraction), and can also be calculated based on the feedstock in the catalyst preparation process.

According to a preferred embodiment of the present invention, based on the total weight of the catalyst; for example, the group VIB metal sulfide calculated in terms of sulfide is contained in an amount of 10-30 wt. %, preferably 15-28 wt. %, the content may be 15 wt. %, 17 wt. %, 20 wt. %, 22 wt. %, 24 wt. %, 26 wt. %, 28 wt. %, or the numerical value within a range consisting of any two values thereof; the group VIII metal sulfide calculated in terms of sulfide is contained in an amount of 2-10 wt. %, preferably 4-8 wt. %, for example, the content may be 4 wt. %, 5 wt. %, 6 wt. %, 7 wt. %, 8 wt. %, or the numerical value within a range consisting of any two values thereof. The hydrogenation catalyst provided by the present invention is a sulfide hydrogenation catalyst, and active components mostly exist in the form of sulfide. The catalyst provided by the present invention does not exclude that the catalyst contains a small amount of group VIB metal oxide and group VIII metal oxide.

The hydrogenation catalyst provided by the present invention may comprise other components, it can be comprehended that the sum of the content of the components in the hydrogenation catalyst is 100%.

According to a preferred embodiment of the present invention, the group VIB metal elements are Mo and/or W, and the group VIII metal elements are Co and/or Ni. Those skilled in the art may select one or more specific active metals to use cooperatively according to the specific field.

In the present invention, the group VIB metal sulfide may refer to $MoS_2$ and $WS_2$, and the group VIII metal sulfide may refer to CoS and NiS.

In the present invention, the contents of group VIB metal sulfide and group VIII metal sulfide can be obtained by joint characterization through the Inductively Coupled Plasma (ICP) and XPS energy spectrum, specifically, the total content of the group VIB metal and the total content of the group VIII metal in the catalyst are initially characterized through ICP, then the contents of the metal elements with different valence states in the catalyst are quantitatively characterized through the XPS energy disperse spectroscopy. The measurement conditions of the XPS energy disperse spectroscopy are as follows: the vacuum degree of the analysis chamber is less than or equal to $5\times10^{-10}$ mbar; the vacuum degree of the preparation chamber is less than or equal to $1\times10^{-7}$ mbar; the double anode sensitivity is $4.5\times10^{6}$, and the energy resolution is 1.0 eV; the monochromator sensitivity is $1.4\times10^{5}$, and the energy resolution is 0.5 eV. The XPSPEAK Version 4.0 is utilized to respectively carry out the fitting and peak separation on the energy spectrum of Mo3d, W4f, Co2p and Ni2p, and the contents of the metal elements with different valence states in the catalyst are obtained through calculation according to the peak areas.

According to a preferred embodiment of the present invention, the molecular sieve is at least one selected from the group consisting of Y-type molecular sieve, ZSM-5 molecular sieve, β-type molecular sieve and MCM-41 molecular sieve. The molecular sieve is commercially available or can be synthesized with a conventional method in the prior art, the present invention is not particularly limited thereto.

The carrier is not particularly limited in the present invention, it may be various carriers conventionally used in the art, it may be a commercially available product or prepared with any method in the prior art, for example, the carrier can be an inorganic refractory oxide. Preferably, the carrier is at least one selected from the group consisting of alumina, silica, titania and zirconia.

Considering the costs and the effects comprehensively, the carrier is preferably alumina.

In the present invention, the carrier may further contain a doping element, and the doping element may be one or more selected from the group consisting of phosphorus, silicon, boron, fluorine, and sodium. The addition amount of the doping element can be a conventional addition amount, and preferably accounts for 0.5-6% of the mass of the carrier.

The second aspect of the present invention provides a preparation method of a hydrogenation catalyst, the method comprises the following steps:

(1) impregnating a carrier with a solution containing an organic auxiliary agent, drying and roasting the carrier in an inert atmosphere to obtain a pretreated carrier;
(2) introducing a VIB group metal salt and a VIII group metal salt into the pretreated carrier through an impregnation method, then sulfurizing the pretreated carrier to obtain a catalyst precursor;
(3) introducing a molecular sieve into the catalyst precursor, subsequently drying and roasting.

According to the method provided by the present invention, the carrier is subjected to the pre-treatment, and an inert C-layer is formed on the carrier surface, on one hand, the C-layer can reduce interaction between the metal and the carrier; on the other hand, during the process of introducing a molecular sieve in step (3), the carrier surface is coated with a C-layer, which belongs to the non-polar layer, more molecular sieve will act on the metal, thereby increasing the percentage of the molecular sieve directly acting on the active metal.

According to a preferred embodiment of the present invention, the carbon content in the pretreated carrier is within a range of 3-20 wt. %, preferably within a range of 5-10 wt. %. The use of such a preferred embodiment not only can increase the percentage of the molecular sieve directly acting on the active metal, but also can ensure the stability of the catalyst.

The present invention does not impose specific limitations to the kind of organic auxiliary agent, as long as it can be dried and roasted in an inert atmosphere to form an inert C-layer on the carrier surface, preferably the organic auxiliary agent is selected from hydrocarbons, alcohols, carboxylic acids, and more preferably, the organic auxiliary agent is at least one selected from the group consisting of ethylene glycol, glycerol, butylene glycol, pentylene glycol, acetic acid, citric acid, glucose, malonic acid, succinic acid and glutaric acid, aviation kerosene and C9 aromatic hydrocarbons.

The organic auxiliary agent preferably has 2-10 carbon atoms. Preferably, the organic auxiliary agent contains a hydroxyl group and/or a carboxyl group, the use of the preferred embodiment is more conducive to the dispersion of the active metal.

According to a preferred embodiment of the present invention, the organic auxiliary agent is at least one selected from the group consisting of ethylene glycol, glycerol, butylene glycol, pentylene glycol, acetic acid, citric acid, glucose, malonic acid, succinic acid and glutaric acid.

According to the method provided by the present invention, the solution containing an organic auxiliary agent further optionally comprises a solvent, it can be understood by those skilled in the art that as long as the inert C-layer is formed on the carrier surface, and the solution containing an organic auxiliary agent as long as can be impregnated on the carrier; when the organic auxiliary agent is a solid organic auxiliary agent, it is preferable that the solution containing an organic auxiliary agent further comprises a solvent; when the organic auxiliary agent is a liquid, the solution containing an organic auxiliary agent may or may not contain a solvent.

According to the present invention, the selection scope of solvent in the solution containing an organic auxiliary agent is wide, it is not specifically limited, as long as the organic auxiliary agent can be dissolved in the solvent (e.g. water or ethanol), those skilled in the art can appropriately choose the solvent according to the kind of the particular organic auxiliary agent.

According to a preferred embodiment of the present invention, the organic auxiliary agent is contained in an amount of 10-30 wt. % in the solution containing an organic auxiliary agent when the organic auxiliary agent is a solid.

According to a preferred embodiment of the present invention, the organic auxiliary agent is contained in an amount of 50-100 wt. % in the solution containing an organic auxiliary agent when the organic auxiliary agent is a liquid.

According to the present invention, the used amount of the solution containing an organic auxiliary agent can be determined according to the pore saturation impregnation.

The inert atmosphere in step (1) of the present invention refers to the atmosphere which does not participate in the reaction, the atmosphere may be provided by an inert gas including but not limited to at least one of nitrogen, helium, argon, and neon.

The drying conditions of step (1) in the present invention preferably comprise a temperature within a range of 20-90° C. and a time of 4-16 hours.

The roasting conditions of step (1) in the present invention preferably comprise a temperature within a range of 200-400° C. and a time of 3-8 hours, more preferably a temperature within a range of 250-350° C. and a time of 3-5 hours.

According to the method provided by the present invention, the selection scope of the types of the carrier and the group VIB metal and group VIII metal can be the same as those of the carrier and the group VIB metal and group VIII metal in the hydrogenation catalyst described in the first aspect mentioned above, the content will not be repeatedly described herein.

In the method provided by the present invention, the impregnation method in step (2) is not particularly limited, it can be an equivalent-volume impregnation or a supersaturation impregnation. The group VIB metal salt and the group VIII metal salt may be simultaneously introduced into a pretreated carrier through the co-impregnation, or may be separately introduced into a pretreated carrier through the stepwise impregnation, the sequence of introducing two metal salts is not particularly limited in the present invention. Preferably, group VIB metal salt and group VIII metal salt may be simultaneously introduced into a pretreated carrier through co-impregnation. Preferably, step (2) comprises a step of impregnating the pretreated carrier with an impregnation solution comprising the group VIB metal salt and the group VIII metal salt, and then drying the impregnated carrier. The method of preparing the impregnation solution is well-known among those skilled in the art. The drying is preferably performed in an inert atmosphere. The selection scope of an inert atmosphere can be the same as that mentioned in the above text, the content will not be repeatedly described herein. The drying conditions comprise a temperature of 20-90° C. and a time of 4-16 hours.

The present invention has a wide selection scope for the types of the group VIB metal salts and group VIII metal salts, as long as the group VIB metal salts and group VIII metal salts can be subsequently converted into the respective metal sulfide; preferably, the group VIB metal salts are phosphate and/or ammonium salts of a group VIB metal, and the group VIII metal salts are at least one selected from the group consisting of nitrates, acetates and sulfates of a group VIII metal.

The sulfurization of step (2) is not particularly limited in the present invention, the sulfurization can be carried out with the conventional methods in the art, as long as the active metal in the oxidation state hydrogenation catalyst is converted to the sulfide state, the generally known sulfurization process; preferably, the sulfurization is a dry sulfurization or a wet sulfurization. The dry sulfurization and the wet sulfurization in the present invention have a general interpretation in the art.

Preferably, the sulfurization conditions comprise: the sulfurization pressure is within a range of 3.2-6.4 MPa, sulfurization temperature is within a range of 250-400° C., the sulfurization time is within a range of 4-12 h, and the flow rate of hydrogen gas is within a range of 2-25 $mL\ min^{-1} \cdot g^{-1}$.

According to a preferred embodiment of the present invention, a dry sulfurization agent used in the dry sulfurization is hydrogen sulfide. concretely, the sulfurization gas used in the dry sulfurization process includes hydrogen sulfide and hydrogen gas. Preferably, a volume content of the hydrogen sulfide in the sulfurization gas is within a range of 1-10%.

According to a preferred embodiment of the present invention, a wet sulfurization agent used in the wet sulfurization is at least one selected from the group consisting of carbon disulfide, dimethyl disulfide, methyl sulfide and n-butyl sulfide. concretely, the sulfurization solution used in the wet sulfurization comprises a wet sulfurization agent and an organic solvent. Preferably, the organic solvent is at least one selected from the group consisting of cyclohexane, n-heptane, aviation kerosene and diesel oil. The mass fraction of the wet sulfurization agent in the sulfurization solution is selected from a wide range, preferably between 2% and 7%, more preferably between 4% and 6%. Preferably, the flow rate of sulfurization solution is within a range of 0.5-5 $mL \cdot h^{-1} \cdot g^{-1}$, preferably within a range of 1-4 $mL \cdot h^{-1} \cdot g^{-1}$.

According to a preferred embodiment of the present invention, the group VIB metal salt and the group VIII metal salt are used in amounts such that the group VIB metal sulfide calculated in terms of sulfide is contained in an amount of 10-30 wt. %, more preferably 15-28 wt. %, and the group VIII metal sulfide calculated in terms of sulfide is contained in an amount of 2-10 wt. %, more preferably 4-8 wt. %, based on the total weight of the catalyst. Those skilled in the art are capable of appropriately selecting the used amounts of the group VIB metal salt and the group VIII metal salt as well as the sulfurization conditions according to the requirements.

According to the present invention, it is preferred that the catalyst precursor and the molecular sieve are used in amounts such that the molecular sieve is contained in an amount of 1-20 wt. %, more preferably 1-12 wt. %, further preferably 1.5-8 wt. %, based on the total weight of the catalyst. The method provided by the present invention comprises a step of adding molecular sieves into the catalyst and enabling the molecular sieves to be loaded on the outer surface of the catalyst rather than kneading with a carrier, on one hand, it is advantageous to increase the percentage of the molecular sieve directly acting on the active metal, and improve the hydrogenation activity of the catalyst; one the other hand, it can precisely control the hydrogenation saturation as well as the ring opening and chain scission activity of the polycyclic aromatic hydrocarbons by controlling the type and content of the molecular sieve, thus the catalyst flexibility is high; and in a third aspect, it increases the utilization ratio of molecular sieves, thereby decreasing the used amount of molecular sieves and reducing the cost of the catalyst.

According to the method of the present invention, the selection scope of the type of molecular sieve in step (3) can be the same as that of the type of molecular sieve in the hydrogenation catalyst according to the first aspect described above, the content is not repeatedly described herein.

According to the method of the present invention, the mode of introducing the molecular sieve into the catalyst precursor in step (3) is not particularly limited, it can be obtained by directly mixing the catalyst precursor with the molecular sieve, or be obtained by mixing the catalyst precursor mixed with the molecular sieve precursor and then subjecting the mixture to a hydrothermal treatment.

Preferably, the step (3) of introducing a molecular sieve into the catalyst precursor is performed by means of at least one of the following modes:

(a) Carrying out a hydrothermal treatment on the catalyst precursor and the molecular sieve precursor, subsequently drying and roasting as described in step (3) in an inert atmosphere;

(b) Blending the catalyst precursor with the ball-milled molecular sieve in the presence of a solvent, subsequently drying and roasting as described in step (3).

According to the present invention, it is understandable that the molecular sieve precursor can be a gel produced through a hydrothermal treatment for preparing the kind of molecular sieve described above. Preferably, the molecular sieve precursor in mode (a) comprises a gel formed by mixing a silicon source and/or an aluminum source, a precipitating agent, a template and water. The preparation method is well-known among those skilled in the art, the molecular sieve can be formed by using a precipitation method or a sol-gel method.

The types of a silicon source and/or an aluminum source, a precipitating agent and a template are well-known among those skilled in the art; the silicon source is preferably at least one selected from the group consisting of sodium silicate, ethyl orthosilicate, silica sol, and chromatographic silica gel. The aluminum source is preferably at least one selected from the group consisting of sodium metaaluminate, aluminum hydroxide, and pseudoboehmite. The precipitating agent is preferably at least one selected from the group consisting of sodium hydroxide, ammonia, and potassium hydroxide. The template is preferably at least one selected from the group consisting of cetyltrimethylammonium bromide, ethylenediamine, n-butylamine, tetrapropylammonium bromide, ethanol, tetraethylammonium hydroxide, tetraethylammonium bromide, triethylamine, di-n-propylamine, di-isopropylamine, and methylcellulose.

According to the present invention, when the molecular sieve is a silica-alumina molecular sieve, preferably, the molar composition of the gel is $n(SiO_2):n(Al_2O_3):n(Na_2O):n(template):n(H_2O)=(5\text{-}30):1:(1\text{-}10):(1\text{-}10):(100\text{-}300)$.

According to the present invention, when the molecular sieve is a pure silica molecular sieve, preferably the molar composition of the gel is $n(SiO_2):n(Na_2O):n(template):n(H_2O)=100:(10\text{-}30):(10\text{-}30):(1,500\text{-}3,000)$.

The hydrothermal treatment conditions according to the present invention are selected from a wide range, as long as the molecular sieve can be obtained. Preferably, the hydrothermal treatment conditions comprise: the temperature is within a range of 90-200° C., the pressure is within a range of 0.1-2 MPa, the pH is within a range of 7.5-9, and the time is within a range of 5-48 hours.

According to the present invention, the ball-milled molecular sieve in the mode (b) preferably has a particle size within a range of 0.1-10 nm, more preferably within a range of 0.1-5 nm. The use of such a preferred embodiment is more advantageous to perform the function of the molecular sieve. The parameters and device of the ball milling are not particularly limited in the present invention.

According to a preferred embodiment of the present invention, the drying conditions in step (3) comprise a temperature within a range of 20-90° C. and a time of 4-16 hours.

According to a preferred embodiment of the present invention, the roasting conditions of step (3) comprise a temperature within a range of 300-500° C. and a time of 2-5 hours.

The drying and roasting of step (3) can be performed in an inert atmosphere. The specific choice of the inert atmosphere can be as described above.

The third aspect of the present invention provides a use of the hydrogenation catalyst according to the first aspect or the hydrogenation catalyst produced with the preparation method according to the second aspect in the oil product hydrogenation.

The hydrogenation catalyst provided by the present invention can be used for the hydrogenation of different oil products by matching different active metals with the molecular sieve types. Preferred applications relate to the use in hydrorefining of oil products, hydrogenation and upgrading of oil products, hydrocracking or special oil hydrorefining, and further preferred application is the use in the polycyclic aromatic hydrocarbon hydrogenation saturation reaction.

The catalyst provided by the present invention has high activity and selectivity, and the catalyst has very high polycyclic aromatic hydrocarbon hydrogenation saturation activity and selectivity when used in the polycyclic aromatic hydrocarbon hydrogenation saturation reaction process.

The fourth aspect of the present invention provides a hydrogenation reaction method for oil products, in particular a method for the polycyclic aromatic hydrocarbon hydrogenation saturation reaction, the method comprises subjecting the oil products to contacting and reacting with the hydrogenation catalyst according to the first aspect or the hydrogenation catalyst produced with the preparation method according to the second aspect.

Preferably, the oil products comprise a polycyclic aromatic hydrocarbon, and the hydrogenation reaction comprises a polycyclic aromatic hydrocarbon hydrogenation saturation reaction. The content of the polycyclic aromatic hydrocarbon in the oil products is preferably within a range of 5-70 wt. %.

The hydrogenation catalyst provided by the present invention is suitable for use in hydrogenation reaction of various oil products containing polycyclic aromatic hydrocarbons, including but not limited to diesel oil.

Preferably, the oil products comprise polycyclic aromatic hydrocarbon in an amount of 10-60 wt. %, monocyclic aromatic hydrocarbon in an amount of 10-30 wt. %, and alkane in an amount of 10-80 wt. %. The oil products may further comprise other elements, such as sulfur and nitrogen, their contents are not particularly limited herein.

Preferably, the reaction conditions comprise: the pressure is within a range of 1-12 MPa, further preferably within a range of 6-10 MPa, a proportion of the hydrogen partial pressure to the total pressure is within a range of 50-90%; the volume space velocity of the oil products is within a range of 0.1-10 $h^{-1}$, further preferably within a range of 0.5-3 $h^{-1}$, the reaction temperature is within a range of 200-400° C., further preferably within a range of 330-380° C., and the volume ratio of hydrogen to oil is within a range of 10-1,000:1, further preferably within a range of 100-800: 1.

The catalysts provided by the present invention and the preparation method and product property of the catalysts are further described below with reference to the examples and comparative examples, but the following examples do not constitute limitations to the method of the present invention.

Among the hydrogenation catalysts in the following examples and comparative examples, the percentage of the amount of the molecular sieve directly acting on a group VIB metal sulfide relative to the total amount of the molecular sieve was characterized by the TEM-EDS (Transmission Electron Microscopy-Energy Dispersive X-ray Spectrum), and the specific method was as described in the DESCRIPTION OF THE PREFERRED EMBODIMENT. The contents of group VIB metal sulfide and group VIII metal sulfide can be obtained by joint characterization through the Inductively Coupled Plasma (ICP) and XPS energy spectrum, the specific method was described in the DESCRIPTION OF THE PREFERRED EMBODIMENT.

Example 1

(1) An alumina carrier was impregnated in an aqueous solution containing 50 wt. % of glycerol, the impregnated alumina carrier was subjected to drying at 80° C. in the $N_2$ atmosphere for 4 h, and then roasting at 300° C. for 3 h to obtain a pretreated carrier, the carbon content of the pretreated carrier was shown in Table 1.

(2) The pretreated carrier prepared in step (1) was impregnated in a solution of nickel nitrate and ammonium heptamolybdate by means of the pore saturation impregnation, the impregnated alumina carrier was subjected to drying at 90° C. in the $N_2$ atmosphere for 3 h, then subjected to a sulfurization treatment by using the hydrogen gas containing 1.5 vol. % of $H_2S$, wherein the flow rate of hydrogen gas was 10 mL $min^{-1} \cdot g^{-1}$, the sulfurization temperature was 290° C., the sulfurization pressure was 3.2 MPa, and the sulfurization time was 4 h, subsequently cooled to room temperature in the $N_2$ atmosphere to obtain a catalyst precursor.

(3) Sodium hydroxide, silica sol, sodium metaaluminate, and ethylenediamine were added into deionized water, wherein the molar ratio of the components was $n(SiO_2)$:n$(Al_2O_3)$:n$(Na_2O)$:n(ethylenediamine):n$(H_2O)$=12:1:6:3:180, the materials were stirred to form a uniform sol, namely the Y-type molecular sieve precursor, the molecular sieve precursor was further blended with the catalyst precursor prepared in step (2), then subjected to the hydrothermal treatment for 10 hours under the conditions comprising a temperature of 150° C., a pressure of 1.0 MPa and pH=8.0; the mixture was subsequently filtered, and washed with deionized water for three times, then subjected to drying at 90° C. in the $N_2$ atmosphere for 3 h and roasting at 450° C. for 3 h to prepare the catalyst C-1.

The catalyst C-1 contained the following components in percentage by weight: 20% of $MoS_2$, 4.2% of NiS, 4.0% of the Y-type molecular sieve, and the balance was alumina carrier.

Figure 2:
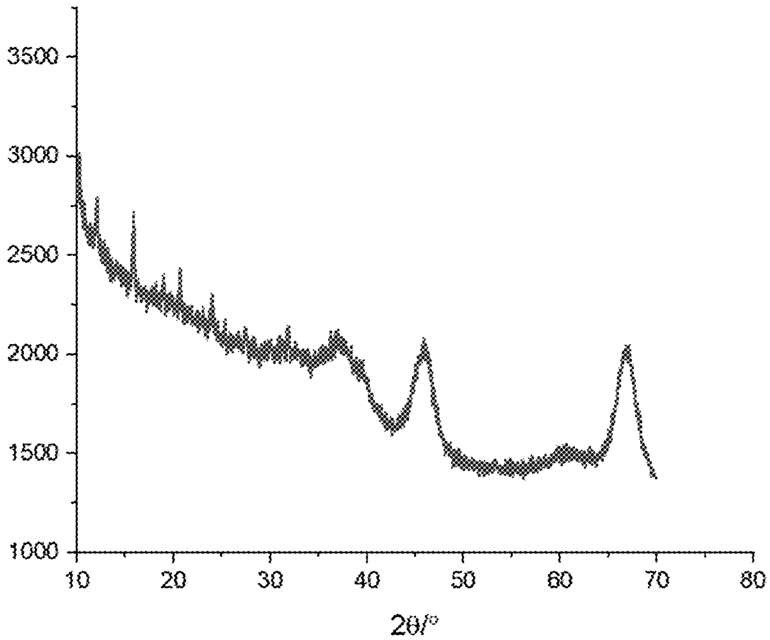
FIG. 2 shows an X-ray diffraction energy spectrum of the catalyst prepared in Example 1 of the present invention.

The TEM image of the catalyst C-1 was shown in FIG. 1, and the XRD image was illustrated in FIG. 2, as can be seen from FIG. 2, the molecular sieve was formed in the catalyst with the method provided by the present invention.

Example 2

(1) An alumina carrier was impregnated in an aqueous solution containing 15 wt. % of glucose, the impregnated alumina carrier was subjected to drying at 90° C. in the $N_2$ atmosphere for 4 h, and then roasting at 350° C. for 3 h to obtain a pretreated carrier, the carbon content of the pretreated carrier was shown in Table 1.

(2) The pretreated carrier prepared in step (1) was impregnated in a solution of nickel nitrate and ammonium heptamolybdate by means of the pore saturation impregnation, the impregnated alumina carrier was subjected to drying at 90° C. in the $N_2$ atmosphere for 3 h, then subjected to a sulfurization treatment by using the hydrogen gas containing 1.5 vol. % of $H_2S$, wherein the flow rate of hydrogen gas was 10 mL $min^{-1} \cdot g^{-1}$, the sulfurization temperature was 300° C., the sulfurization pressure was 3.2 MPa, and the sulfurization time was 4 h, subsequently cooled to room temperature in the $N_2$ atmosphere to obtain a catalyst precursor.

(3) Sodium hydroxide, silica sol, sodium metaaluminate and ethylenediamine were added into deionized water, was wherein the molar ratio of the components $n(SiO_2)$:n$(Al_2O_3)$:n$(Na_2O)$:n(n-butylamine):n$(H_2O)$=20:1:7:6:200, the materials were stirred to form a uniform sol, namely the ZSM-5 molecular sieve precursor, the molecular sieve precursor was further blended with the catalyst precursor prepared in step (2), then subjected to the hydrothermal treatment for 20 hours under the conditions comprising a temperature of 120° C., a pressure of 1.0 MPa and pH=8.5; the mixture was subsequently filtered, and washed with deionized water for three times, then subjected to drying at 90° C. in the $N_2$ atmosphere for 3 h and roasting at 450° C. for 3 h to prepare the catalyst C-2.

The catalyst C-2 contained the following components in percentage by weight: 21% of $MoS_2$, 4.2% of NiS, 3.5% of the ZSM-5 molecular sieve, and the balance was alumina carrier.

Example 3

(1) An alumina carrier was impregnated in an aqueous solution containing 50 wt. % of ethylene glycol, the impregnated alumina carrier was subjected to drying at 90° C. in the $N_2$ atmosphere for 4 h, and then roasting at 300° C. for 3 h to obtain a pretreated carrier, the carbon content of the pretreated carrier was shown in Table 1.

(2) The pretreated carrier prepared in step (1) was impregnated in a solution of nickel nitrate and ammonium heptamolybdate by means of the pore saturation impregnation, the impregnated alumina carrier was subjected to drying at 90° C. in the $N_2$ atmosphere for 3 h, then subjected to a sulfurization treatment by using the hydrogen gas containing 1.5 vol. % of $H_2S$, wherein the flow rate of hydrogen gas was 10 mL $min^{-1}\cdot g^{-1}$, the sulfurization temperature was 290° C., the sulfurization pressure was 3.0 MPa, and the sulfurization time was 4 h, subsequently cooled to room temperature in the $N_2$ atmosphere to obtain a catalyst precursor.

(3) Sodium metaaluminate and sodium hydroxide were dissolved in deionized water, tetraethylammonium bromide was then added, and stirred violently, silica sol was slowly and dropwise added, then subjected to aging for 3 h, wherein the molar ratio of the components was $n(SiO_2)$:$n(Al_2O_3)$:$n(Na_2O)$:n(tetraethylammonium bromide):$n(H_2O)$=25:1:6:5:250, the β-type molecular sieve precursor was formed, the molecular sieve precursor was further blended with the catalyst precursor prepared in step (2), then subjected to the hydrothermal treatment for 15 hours under the conditions comprising a temperature of 130° C., a pressure of 1.0 MPa and pH=8.5; the mixture was subsequently filtered, and washed with deionized water for three times, then subjected to drying at 90° C. in the $N_2$ atmosphere for 3 h and roasting at 450° C. for 3 h to prepare the catalyst C-3.

The catalyst C-3 contained the following components in percentage by weight: 24% of $MoS_2$, 3.2% of NiS, 5.0% of the β-type molecular sieve, and the balance was alumina carrier.

Example 4

(1) An alumina carrier was impregnated in an aqueous solution containing 50 wt. % of ethylene glycol, the impregnated alumina carrier was subjected to drying at 90° C. in the $N_2$ atmosphere for 4 h, and then roasting at 250° C. for 3 h to obtain a pretreated carrier, the carbon content of the pretreated carrier was shown in Table 1.

(2) The pretreated carrier prepared in step (1) was impregnated in a solution of nickel nitrate and ammonium heptamolybdate by means of the pore saturation impregnation, the impregnated alumina carrier was subjected to drying at 90° C. in the $N_2$ atmosphere for 3 h, then subjected to a sulfurization treatment by using the hydrogen gas containing 1.5 vol. % of $H_2S$, wherein the flow rate of hydrogen gas was 10 mL $min^{-1}\cdot g^{-1}$, the sulfurization temperature was 300° C., the sulfurization pressure was 3.0 MPa, and the sulfurization time was 4 h, subsequently cooled to room temperature in the $N_2$ atmosphere to obtain a catalyst precursor.

(3) Hexadecyl trimethyl ammonium bromide was mixed with sodium hydroxide, the mixture was added into deionized water and stirred, ethyl orthosilicate was then dropwise added into the mixed solution, subsequently stirred for 30 min, wherein the molar ratio of the components was $n(SiO_2)$:$n(Na_2O)$:n(hexadecyl trimethyl ammonium bromide):$n(H_2O)$=11:2:2:200, the MCM-41 molecular sieve precursor was formed, the molecular sieve precursor was further blended with the catalyst precursor prepared in step (2), then subjected to the hydrothermal treatment for 15 hours under the conditions comprising a temperature of 130° C., a pressure of 1.0 MPa and pH=8.5; the mixture was subsequently filtered, and washed with deionized water for three times, then subjected to drying at 80° C. in the $N_2$ atmosphere for 3 h, and roasting at 500° C. for 3 h to prepare the catalyst C-4.

The catalyst C-4 contained the following components in percentage by weight: 22% of $MoS_2$, 4.8% of NiS, 3.8% of the MCM-41 molecular sieve, and the balance was alumina carrier.

Example 5

(1) An alumina carrier was impregnated in a solution containing 100 wt. % of aviation kerosene (atmospheric distillation fraction with the distillation range of 100-220° C.), and the impregnated alumina carrier was subjected to drying at 80° C. in the $N_2$ atmosphere for 4 h, and then roasting at 350° C. for 3 h to obtain a pretreated carrier, the carbon content of the pretreated carrier was shown in Table 1.

(2) The pretreated carrier prepared in step (1) was impregnated in a solution of cobalt nitrate and ammonium heptamolybdate by means of the pore saturation impregnation, the impregnated alumina carrier was subjected to drying at 90° C. in the $N_2$ atmosphere for 3 h, then subjected to a sulfurization treatment by using the hydrogen gas containing 1.5 vol. % of $H_2S$, wherein the flow rate of hydrogen gas was 10 mL $min^{-1}\cdot g^{-1}$, the sulfurization temperature was 300° C., the sulfurization pressure was 3.2 MPa, and the sulfurization time was 4 h, subsequently cooled to room temperature in the $N_2$ atmosphere to obtain a catalyst precursor.

(3) Sodium hydroxide, silica sol, sodium metaaluminate, and ethylenediamine were added into deionized water, wherein the molar ratio of the components was $n(SiO_2)$:$n(Al_2O_3)$:$n(Na_2O)$:n(ethylenediamine):$n(H_2O)$=12:1:6:3:180, the materials were stirred to form a uniform sol, namely the Y-type molecular sieve precursor, the molecular sieve precursor was further blended with the catalyst precursor prepared in step (2), then subjected to the hydrothermal treatment for 15 hours under the conditions comprising a temperature of 150° C., a pressure of 1.0 MPa and pH-9.0; the mixture was subsequently filtered, and washed with deionized water for three times, then subjected to drying at 80° C. in the $N_2$ atmosphere for 3 h and roasting at 450° C. for 3 h to prepare the catalyst C-5.

The catalyst C-5 contained the following components in percentage by weight: 20% of $MoS_2$, 5.0% of CoS, 5.0% of the Y-type molecular sieve, and the balance was alumina carrier.

Example 6

(1) An alumina carrier was impregnated in an aqueous solution containing 30 wt. % of glucose, the impregnated alumina carrier was subjected to drying at 90° C. in the $N_2$ atmosphere for 4 h, and then roasting at 350° C. for 3 h to obtain a pretreated carrier, the carbon content of the pretreated carrier was shown in Table 1.

(2) The pretreated carrier prepared in step (1) was impregnated in a solution of nickel nitrate and ammonium metatungstate by means of the pore saturation impregnation, the impregnated alumina carrier was subjected to drying at 80° C. in the $N_2$ atmosphere for 3 h, then subjected to a sulfurization treatment by using the hydrogen gas containing 1.5 vol. % of $H_2S$, wherein the flow rate of hydrogen gas was 10 mL $min^{-1}\cdot g^{-1}$, the sulfurization temperature was 300° C., the sulfurization pressure was 3.0 MPa, and the sulfurization time was 4 h, subsequently cooled to room temperature in the $N_2$ atmosphere to obtain a catalyst precursor.

(3) Sodium hydroxide, silica sol, sodium metaaluminate, and ethylenediamine were added into deionized water, wherein the molar ratio of the components was $n(SiO_2):n(Al_2O_3):n(Na_2O):n(\text{n-butylamine}):n(H_2O)=20:1:7:6:200$, the materials were stirred to form a uniform sol, namely the ZSM-5 molecular sieve precursor, the molecular sieve precursor was further blended with the catalyst precursor prepared in step (2), then subjected to the hydrothermal treatment for 15 hours under the conditions comprising a temperature of 130° C., a pressure of 1.0 MPa and pH=8.5; the mixture was subsequently filtered, and washed with deionized water for three times, then subjected to drying at 80° C. in the $N_2$ atmosphere for 3 h, and roasting at 450° C. for 3 h to prepare the catalyst C-6.

The catalyst C-6 contained the following components in percentage by weight: 24% of $WS_2$, 4.8% of NiS, 4.3% of the ZSM-5 molecular sieve, and the balance was alumina carrier.

Example 7

(1) An alumina carrier was impregnated in an aqueous solution containing 30 wt. % of glucose, the impregnated alumina carrier was subjected to drying at 90° C. in the $N_2$ atmosphere for 4 h, and then roasting at 300° C. for 3 h to obtain a pretreated carrier, the carbon content of the pretreated carrier was shown in Table 1.

(2) The pretreated carrier prepared in step (1) was impregnated in a solution of cobalt nitrate and ammonium metatungstate by means of the pore saturation impregnation, the impregnated alumina carrier was subjected to drying at 90° C. in the $N_2$ atmosphere for 3 h, then subjected to a sulfurization treatment by using the hydrogen gas containing 1.5 vol. % of $H_2S$, wherein the flow rate of hydrogen gas was 10 mL $min^{-1}\cdot g^{-1}$, the sulfurization temperature was 320° C., the sulfurization pressure was 3.0 MPa, and the sulfurization time was 4 h, subsequently cooled to room temperature in the $N_2$ atmosphere to obtain a catalyst precursor.

(3) Sodium hydroxide, silica sol, sodium metaaluminate, and ethylenediamine were added into deionized water, wherein the molar ratio of the components was $n(SiO_2):n(Al_2O_3):n(Na_2O):n(\text{n-butylamine}):n(H_2O)=12:1:6:3:180$, the materials were stirred to form a uniform sol, namely the Y-type molecular sieve precursor, the molecular sieve precursor was further blended with the catalyst precursor prepared in step (2), then subjected to the hydrothermal treatment for 15 hours under the conditions comprising a temperature of 130° C., a pressure of 1.0 MPa and pH-8.5; the mixture was subsequently filtered, and washed with deionized water for three times, then subjected to drying at 90° C. in the $N_2$ atmosphere for 3 h and roasting at 450° C. for 3 h to prepare the catalyst C-7.

The catalyst C-7 contained the following components in percentage by weight: 24% of $WS_2$, 4.8% of CoS, 5.0% of the Y-type molecular sieve, and the balance was alumina carrier.

Example 8

The catalyst was prepared according to the same method as that in Example 1, except that the alumina carrier was replaced with zirconia to obtain the catalyst C-8.

Example 9

The catalyst was prepared according to the same method as that in Example 1, except that in step (3), the catalyst precursor prepared in step (2) was directly mixed with the ball-milled Y-type molecular sieve (with a particle size of 0.2-2.0 nm), the mixture was then subjected to the drying and roasting. The preparation of the Y-type molecular sieve comprised the following steps: sodium hydroxide, silica sol, sodium metaaluminate, and ethylenediamine were added into deionized water, wherein the molar ratio of the components was $n(SiO_2):n(Al_2O_3):n(Na_2O):n(\text{ethylenediamine}):n(H_2O)=12:1:6:3:180$, the materials were stirred to form a uniform sol, then subjected to the hydrothermal treatment for 10 hours under the conditions comprising a temperature of 150° C., a pressure of 1.0 MPa and pH-8.0; subsequently filtered, and washed with deionized water for three times, then subjected to drying at 90° C. in the $N_2$ atmosphere for 3 h and roasting at 450° C. for 3 h to prepare the catalyst C-9.

Example 10

The catalyst was prepared according to the same method as that in Example 1, except that the molecular sieve content was 16%, the $MoS_2$ and NiS contents were unchanged, the alumina carrier content was correspondingly reduced, and the catalyst C-10 was obtained.

Comparative Example 1

(1) The Y-type molecular sieve were uniformly mixed with alumina powder, nitric acid, starch, and deionized water, wherein the mass ratio of the Y-type molecular sieve:alumina powder:nitric acid:starch:deionized water was 8:92:4:3:60, the mixture was then subjected to kneading and extrusion molding, the extruded strips were then subjected to drying at 80° C. for 10 hours, and roasting at 650° C. for 3 h, so as to obtain the modified alumina carrier, wherein the content of the Y-type molecular sieve was 8%.

(2) The modified alumina carrier prepared in step (1) was impregnated in a mixed solution of phosphomolybdic acid and nickel nitrate, the impregnated alumina carrier was subjected to drying at 90° C. for 3 h and roasting at 450° C. for 3 h, then subjected to a sulfurization treatment, wherein the sulfurization temperature was 320° C., the sulfurization pressure was 3.0 MPa, and the sulfurization time was 4 h, subsequently cooled to room temperature in the $N_2$ atmosphere to obtain a catalyst DC-1.

The catalyst DC-1 contained the following components in percentage by weight: 20% of $MoS_2$, 4.8% of NiS, 6% of the Y-type molecular sieve, and the balance was alumina.

Comparative Example 2

(1) An alumina carrier was impregnated in a mixed solution of cobalt nitrate and ammonium metatungstate, the impregnated alumina carrier was subjected to drying at 90° C. in the $N_2$ atmosphere for 3 h, then subjected to a sulfurization treatment by using the hydrogen gas containing 1.5 vol. % of $H_2S$, wherein the sulfurization temperature was 320° C., the sulfurization pressure was 3.0 MPa, and the sulfurization time was 4 h, subsequently cooled to room temperature in the $N_2$ atmosphere to obtain a catalyst precursor.

(2) Sodium hydroxide, silica sol, sodium metaaluminate, and ethylenediamine were added into deionized water, wherein the molar ratio of the components was $n(SiO_2):n(Al_2O_3):n(Na_2O):n(\text{ethylenediamine}):n(H_2O)=12:1:6:3:180$, the materials were stirred to form a uniform sol, namely the Y-type molecular sieve precursor, the molecular sieve precursor was further blended with the catalyst precursor prepared in step (2), then subjected to the hydrothermal treatment for 15 hours under the conditions comprising a temperature of 130° C., a pressure of 1.0 MPa and pH-8.5; the mixture was subsequently filtered, and washed with deionized water for three times, then subjected to drying at 90° C. in the $N_2$ atmosphere for 3 h to prepare the catalyst DC-2.

The catalyst DC-2 contained the following components in percentage by weight: 24% of $WS_2$, 4.8% of CoS, 5.0% of the Y-type molecular sieve, and the balance was alumina carrier.

Comparative Example 3

(1) An alumina carrier was impregnated in an aqueous solution containing 30 wt. % of glucose, the impregnated alumina carrier was subjected to drying at 90° C. in the $N_2$ atmosphere for 4 h, and then roasting at 300° C. for 3 h to obtain a pretreated carrier.

(2) The pretreated carrier prepared in step (1) was impregnated in a solution of cobalt nitrate and ammonium metatungstate, the impregnated alumina carrier was subjected to drying at 80° C. in the $N_2$ atmosphere for 3 h, then roasting at 400° C. for 3 h to obtain a catalyst precursor.

(3) Sodium hydroxide, silica sol, sodium metaaluminate and ethylenediamine were added into deionized water, wherein the molar ratio of the components was $n(SiO_2):n(Al_2O_3):n(Na_2O):n(\text{ethylenediamine}):n(H_2O)=12:1:6:3:180$, the materials were stirred to form a uniform sol, namely the Y-type molecular sieve precursor, the molecular sieve precursor was further blended with the catalyst precursor prepared in step (2), then subjected to the hydrothermal treatment for 15 hours under the conditions comprising a temperature of 130° C., a pressure of 1.0 MPa and pH-8.5; the mixture was subsequently filtered, and washed with deionized water for three times, then subjected to drying at 90° C. in the $N_2$ atmosphere for 3 h, and roasting at 450° C. for 3 h, then subjected to a sulfurization treatment by using the hydrogen gas containing 1.5 vol. % of $H_2S$, wherein the sulfurization temperature was 320° C., the sulfurization pressure was 3.0 MPa, and the sulfurization time was 4 h, subsequently cooled to room temperature in the $N_2$ atmosphere to prepare the catalyst DC-3.

The catalyst DC-3 contained the following components in percentage by weight: 24% of $WS_2$, 4.8% of CoS, 5.0% of the Y-type molecular sieve, and the balance was alumina carrier.

In the above Examples and Comparative Examples, the percentage of the amount of the molecular sieve directly acting on a group VIB metal sulfide relative to the total amount of the molecular sieve based on the silicon element was shown in Table 1.

TABLE 1

| Table 1Catalyst No. | Carbon content of the pretreated carrier, wt. % | Percentage of the amount of the molecular sieve directly acting on a group VIB metal sulfide to the total amount of the molecular sieve, % |
|---|---|---|
| C-1 | 6.2 | 74 |
| C-2 | 5.1 | 81 |
| C-3 | 6.7 | 86 |
| C-4 | 6.7 | 82 |
| C-5 | 9.5 | 76 |
| C-6 | 8.2 | 83 |
| C-7 | 8.9 | 75 |
| C-8 | 5.8 | 68 |
| C-9 | Same as Example 1 | 66 |
| C-10 | Same as Example 1 | 62 |
| DC-1 | — | 35 |
| DC-2 | — | 51 |
| DC-3 | 8.2 | 57 |

Application Example 1

The application example illustrated the hydrogenation property of the catalysts provided by the present invention for polycyclic aromatic hydrocarbon in diesel.

The raw oil adopted for evaluation was the diesel feedstock provided by a refinery of the China Petroleum and Chemical Corporation (Sinopec Group), and the main properties of the raw oil were as follows: the distillation range was 200-380° C., the sulfur content was 1.5 wt %, the nitrogen content was 580 μg/g, the monocarboxylic aromatic hydrocarbon content was 20 wt. %, and the polycyclic aromatic hydrocarbon content was 26 wt. %. The catalysts provided in Examples and Comparative Examples were subjected to hydrogenation reaction performance evaluation by using a 200 mL fixed bed hydrogenation unit. The evaluation reaction conditions were as follows: the operating pressure was 6.4 MPa, the reaction temperature was 370° C., the hydrogen/oil volume ratio was 600:1, the volume space velocity was 1.2 $h^{-1}$, and the evaluation results after the reaction for 100 h were shown in Table 2.

TABLE 2

| | Product distribution, m % | | | |
|---|---|---|---|---|
| Catalyst No. | The yield of naphtha, % (45-200° C.) | Yield of diesel, % (200-360° C.) | Content of monocyclic aromatic hydrocarbon in diesel, % | Content of polycyclic aromatic hydrocarbon in diesel, % |
| C-1 | 9.1 | 85.9 | 41.2 | 4.8 |
| C-2 | 12.1 | 82.9 | 40.6 | 5.4 |
| C-3 | 18.5 | 76.5 | 42.2 | 3.8 |
| C-4 | 13.1 | 81.9 | 40.9 | 5.1 |
| C-5 | 11.3 | 84.7 | 39.7 | 6.3 |
| C-6 | 13.1 | 82.9 | 41.8 | 4.2 |
| C-7 | 10.2 | 83.8 | 38.9 | 7.1 |
| C-8 | 8.8 | 90.2 | 40.2 | 5.8 |
| C-9 | 8.7 | 88.3 | 40.1 | 5.9 |
| C-10 | 7.9 | 89.1 | 39.9 | 6.1 |
| DC-1 | 0.7 | 98.1 | 28.7 | 17.3 |
| DC-2 | 1.0 | 95.9 | 29.8 | 16.2 |
| DC-3 | 3.2 | 94.8 | 33.8 | 12.2 |

Application Example 2

The application example illustrated the hydrogenation property of the catalysts provided by the present invention for catalyzing polycyclic aromatic hydrocarbon in diesel.

The raw oil adopted for evaluation was the catalytic diesel oil provided by a refinery of the Sinopec Group, and the main properties of the raw oil were as follows: the distillation range was 200-380° C., the sulfur content was 2.5 wt %, the nitrogen content was 1,050 μg/g, the monocarboxylic aromatic hydrocarbon content was 20 wt. %, and the polycyclic aromatic hydrocarbon content was 55 wt. %. The catalysts provided in Examples 2, 3 and 4 were subjected to hydrogenation reaction performance evaluation by using a 200 mL fixed bed hydrogenation unit. The evaluation reaction conditions were as follows: the operating pressure was 8.4 MPa, the reaction temperature was 360° C., the hydrogen/oil volume ratio was 800:1, the volume space velocity was 1.0 $h^{-1}$, and the evaluation results after the reaction for 100 h were shown in Table 3.

TABLE 3

| | Product distribution, m % | | | |
|---|---|---|---|---|
| Catalyst No. | The yield of naphtha, % (45-200° C.) | Yield of diesel, % (200-360° C.) | Content of monocyclic aromatic hydrocarbon in diesel, % | Content of polycyclic aromatic hydrocarbon in diesel, % |
| C-2 | 6.1 | 92.6 | 59.3 | 8.4 |
| C-3 | 12.5 | 86.5 | 60.4 | 6.8 |
| C-4 | 7.1 | 91.8 | 58.6 | 8.1 |

The invention claimed is:

1. A hydrogenation catalyst, characterized in that the hydrogenation catalyst is a sulfurized hydrogenation catalyst and comprises a carrier, a molecular sieve and an active component, wherein the active component comprises at least one of group VIII metal elements and at least one of group VIB metal elements, and, wherein, determined using a Transmission Electron Microscopy—Energy Dispersive X-ray Spectrum (TEM-EDS) method, on the basis of the silicon element, the percentage of the amount of the molecular sieve directly acting on a group VIB metal sulfide relative to the total amount of the molecular sieve is within a range of 60-100%.

2. The catalyst according to claim 1, wherein on the basis of the silicon element, the percentage of the amount of the molecular sieve directly acting on the group VIB metal sulfide relative to the total amount of the molecular sieve is within a range of 65-95%.

3. The catalyst according to claim 1, wherein the molecular sieve is in an amount of 1-20 wt. %, based on the total weight of the catalyst.

4. The catalyst according to claim 1, wherein the group VIB metal sulfide calculated in terms of sulfide is in an amount of 10-30 wt. %; and a group VIII metal sulfide calculated in terms of sulfide is in an amount of 2-10 wt. %, based on the total weight of the catalyst.

5. The catalyst according to claim 1, wherein the at least one of group VIB metal elements are Mo and/or W, the group VIII metal elements are Co and/or Ni;

the molecular sieve is at least one selected from the group consisting of Y-type molecular sieve, ZSM-5 molecular sieve, β-type molecular sieve and MCM-41 molecular sieve;

the carrier is at least one selected from the group consisting of alumina, silica, titania and zirconia.

6. A preparation method of a hydrogenation catalyst according to claim 1, comprising:

(1) impregnating a carrier with a solution containing an organic auxiliary agent, drying and roasting the carrier in an inert atmosphere to obtain a pretreated carrier;

(2) introducing a VIB group metal salt and a VIII group metal salt into the pretreated carrier through an impregnation method, then sulfurizing the pretreated carrier to obtain a catalyst precursor; and (3) introducing a molecular sieve into the catalyst precursor, and subsequently drying and roasting.

7. The preparation method according to claim 6, wherein the carbon content in the pretreated carrier is within a range of 3-20 wt. %.

8. The preparation method according to claim 6, wherein the organic auxiliary agent in step (1) has 2-10 carbon atoms; and the organic auxiliary agent contains a hydroxyl group and/or a carboxyl group.

9. The preparation method according to claim 6, wherein the carrier is at least one selected from the group consisting of alumina, silica, titania, and zirconia; and the group VIB metal elements are Mo and/or W, the group VIII metal elements are Co and/or Ni.

10. The preparation method according to claim 6, wherein the group VIB metal salt and the group VIII metal salt are used in amounts such that the group VIB metal sulfide calculated in terms of sulfide is contained in an amount of 10-30 wt. %; and the group VIII metal sulfide calculated in terms of sulfide is contained in an amount of 2-10 wt. %, based on the total weight of the catalyst.

11. The preparation method according to claim 6, wherein the sulfurization of step (2) is a dry sulfurization using hydrogren sulfide, or a wet sulfurization using a wet sulfurization agent that is at least one selected from the group consisting of carbon disulfide, dimethyl disulfide, methyl sulfide, and n-butyl sulfide.

12. The preparation method according to claim 6, wherein the sulfurization conditions in step (2) comprise: the sulfurization pressure is within a range of 3.2-6.4 MPa, the sulfurization temperature is within a range of 250-400° C., the sulfurization time is within a range of 4-12 h, and the flow rate of hydrogen gas is within a range of 2-25 $mL \cdot min^{-1} \cdot g^{-1}$.

13. The preparation method according to claim 6, wherein the catalyst precursor and the molecular sieve are used in amounts such that the molecular sieve is contained in an amount of 1-20 wt. %, based on the total weight of the catalyst.

14. The preparation method according to claim 6, wherein the molecular sieve is at least one selected from the group consisting of Y-type molecular sieve, ZSM-5 molecular sieve, β-type molecular sieve, and MCM-41 molecular sieve.

15. The preparation method according to claim 6, wherein the step (3) of introducing a molecular sieve into the catalyst precursor is performed by means of at least one of the following modes:

(a) carrying out a hydrothermal treatment on the catalyst precursor and the molecular sieve precursor, subsequently drying and roasting as described in step (3) in an inert atmosphere;

(b) blending the catalyst precursor with the ball-milled molecular sieve in the presence of a solvent, subsequently drying and roasting as described in step (3).

16. The preparation method according to claim 15, wherein the molecular sieve precursor in mode (a) comprises a gel formed by mixing a silicon source and/or an aluminum source, a precipitating agent, a template, and water;

and/or, the hydrothermal treatment conditions comprise: the temperature is within a range of 90-200° C., the pressure is within a range of 0.1-2 MPa, the pH is within a range of 7.5-9, and the time is within a range of 5-48 hours.

17. The preparation method according to claim 15, wherein the ball-milled molecular sieve in mode (b) has a particle size within a range of 0.1-10 nm.

18. A hydrogenation reaction method for an oil product, the method comprises subjecting the oil product to contacting and reacting with the hydrogenation catalyst according to claim 1.

19. The hydrogenation reaction method according to claim 18, wherein the oil product comprise a polycyclic aromatic hydrocarbon, and the hydrogenation reaction comprises a polycyclic aromatic hydrocarbon hydrogenation saturation reaction.

20. The hydrogenation reaction method according to claim 18, wherein the reacting is carrying out under reaction conditions comprising: the pressure is within a range of 1-12 MPa, a proportion of the hydrogen partial pressure to the total pressure is within a range of 50-90%; the volume space velocity of the oil products is within a range of 0.1-10 h-1, the reaction temperature is within a range of 200-400° C., and the volume ratio of hydrogen to oil is within a range of 10-1,000:1.

* * * * *